United States Patent [19]

Spector et al.

[11] Patent Number: 4,762,780
[45] Date of Patent: Aug. 9, 1988

[54] METHOD AND COMPOSITION FOR SCREENING AND DIAGNOSING "HCMV"

[75] Inventors: Deborah H. Spector; Stephen A. Spector, both of Encinitas, Calif.

[73] Assignee: The Regents of the University of California, Berkeley, Calif.

[21] Appl. No.: 4,291

[22] Filed: Jan. 5, 1987

Related U.S. Application Data

[63] Continuation of Ser. No. 601,094, Apr. 17, 1984, abandoned, which is a continuation of Ser. No. 438,662, Nov. 2, 1982, abandoned.

[51] Int. Cl.$^4$ .................. C12Q 1/68; C12Q 1/70; C12P 19/34; C12N 15/00
[52] U.S. Cl. ........................... 435/6; 435/5; 435/91; 435/172.1; 435/172.3; 436/94; 536/27; 935/78
[58] Field of Search ............. 435/5, 6, 68, 70, 91, 435/172.1, 172.3, 253, 317, 320; 536/27; 935/78; 436/63, 94, 501, 504

[56] References Cited

U.S. PATENT DOCUMENTS 4,302,204 11/1981 Wahl et al. ........................... 435/6
4,358,535 11/1982 Falkow et al. ....................... 435/6

OTHER PUBLICATIONS

Huang et al., "Cytomegalovirus D.N.A. and Adenocarcinoma of the Colon: Evidence for Latent Viral Infection", The Lancet, May 6, 1978, pp. 957–960.
Southern, "Detection of Specific Sequences Among DNA Fragments Separated by Gel Electrophoresis", J. Mol. Biol. 98: 503 (1975).
Fleckenstein et al., "Cloning of the Complete Human Cytomegalovirus Genome in Cosmids", Gene 18: 39 (1982).
Oram et al., "Use of Recombinant Plasmids to Investigate the Structure of the Human Cytomegalovirus Genome", J. Gen. Virol. 59: 111 (1982).
Demarchi, "Human Cytomegalovirus DNA: Restriction Enzyme Cleavage Maps and Map Locations for Immediate-Early, Early, and Late RNAs", Virol. 114: 23 (1981).
Westrate et al.; "Human Cytomegalovirus DNA: Physical Maps for the Restriction Endonucleases Bgl II, Hind III, and Xba I", J. Gen. Virol. 49: 1 (1980).
Tamashiro et al., "Molecular Cloning of the Human Cytomegalovirus Genome (Strain AD169)", Chem. Abstr. 94: 117625q (1981) of ICN-UCLA Symp. Mol. Cell. Biol. 18: 21 (1980).
Denhardt, "A Membrane-Filter Technique for the Detection of Complementary DNA", Biochem. Biophys. Res. Comm. 23: 641 (1966).
Grunstein et al., "Colony Hybridization: A Method for the Isolation of Cloned DNAs that Contain a Specific gene", Proc. Natl. Acad. Sci. U.S.A. 72: 3961 (1975).
Chou et al., Abstr. of the 1982 ICAAC, Oct. 4–6, 1982, Miami, Fla., p. 96, item 180.
Spector et al., *J. Virol.* (1982) 42:558–582.
Tamashiro et al., *J. Virol.* (1982) 42:547–557.
Huang And Pagano, *Methods in Virology,* Marramore & Kaprowski, Eds., New York, 1977, pp. 457–497.

*Primary Examiner*—James Martinell
*Attorney, Agent, or Firm*—Bertram I. Rowland

[57] ABSTRACT

DNA sequences of hCMV are obtained by restriction of the hCMV genome, the resulting fragments free of fragments cross-hybridizing with human DNA and other viruses may be used for hybridization with clinical samples suspected of containing hCMV to provide a sensitive method for detection of hCMV at low particle number.

22 Claims, 1 Drawing Sheet

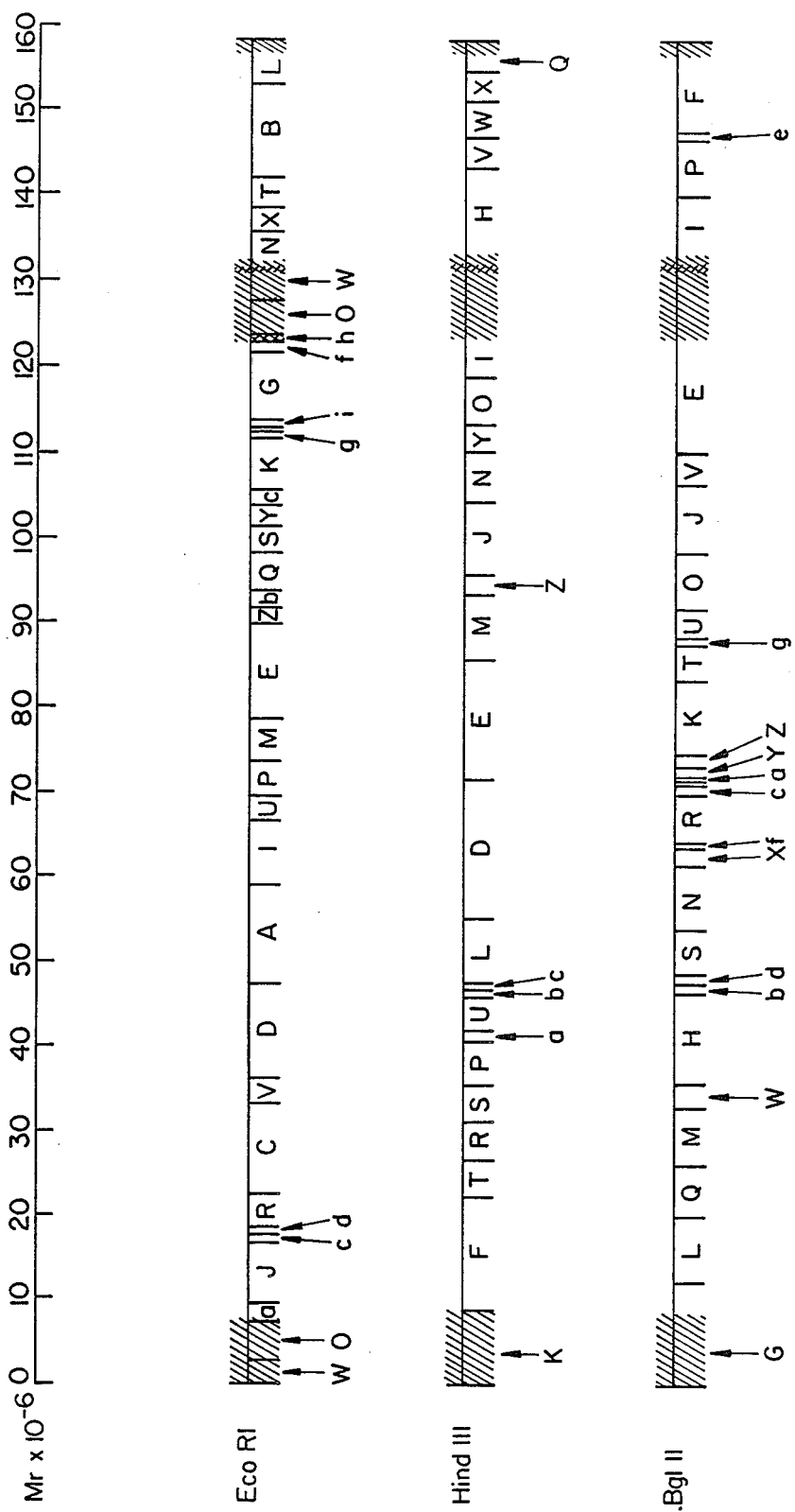
FIGURE

METHOD AND COMPOSITION FOR SCREENING AND DIAGNOSING "HCMV"

This invention was made with Government support under Grant No. AI 15635 awarded by the Department of Health and Human Services. The Government has certain rights in this invention.

This is a continuation of application Ser. No. 601,094, filed Apr. 17, 1984, now abandoned, which is a continuation of application Ser. No. 438,662, filed Nov. 2, 1982, now abandoned.

BACKGROUND OF THE INVENTION

1. Field of the Invention

Cytomegalovirus is a double stranded DNA virus, approximately 240,000 nucleotides in length, belonging to the herpesvirus group. Human cytomegalovirus ("hCMV") has become increasingly involved in a wide of variety of diseased states. In the United States, hCMV infects in utero about 1% of all newborns and is currently the most common infectious cause of birth defects. hCMV infections have a major impact on immunocompromised patients. There is abundant data to indicate that hCMV is considerably more virulent than other viral agents in patients undergoing immunosuppression. Both animal and human studies suggest that CMV is latent in white blood cells. Many herpesviruses appear to have oncogenic properties.

At present, there is no effective CMV vaccine and no antiviral therapy is available. Definitive diagnosis of CMV infections is made by growing the virus in tissue culture, which may take as long as six weeks. In many situations, the early diagnosis of hCMV could be important in the prevention of a seriously malformed neonate, where the mother is compromised by CMV. A simple, rapid and accurate screening technique is essential for detecting CMV during pregnancy, with immunosuppressed patients, and in the detection of blood donors capable of transmitting hCMV.

2. Description of the Prior Art

Tamashiro et al., J. Virology (1982) 42:547-557 describe a construction of a cloned library of EcoRI fragments from the hCMV genome. Spector et al., Ibid. (1982) 42:558-582 describe restriction cleavage maps for hCMV DNA strain AD169. See also references cited therein. Chou and Merigan, Abstracts of the 22nd Interscience Conference on Antimicrobial Agents and Chemotherapy 4-6 Oct., 1982, Miami Beach, FLA. p. 96, item 180, describe the use of a CMV fragment (O) to detect CMV in urine specimens.

SUMMARY OF THE INVENTION

Methods and compositions are provided for detecting human cytomegalovirus infection. The method employs at least one fragment from the hCMV genome which is diagnostic for hCMV but does not cross-hybridize with human DNA or other viruses. The fragments are hybridized with DNA from a sample suspected of containing the virus and any means for detecting duplexes having the necessary sensitivity may be employed.

DESCRIPTION OF THE DRAWING

The figure is a restriction map of the hCMV genome strain AD169 for the restriction endonucleases EcoRI, HindIII, and BglII.

DESCRIPTION OF THE SPECIFIC EMBODIMENTS

Methods and compositions are provided for the sensitive detection of infection of a human host with human cytomegalovirus ("hCMV"). The method involves combining under stringent hybridization conditions at least one, usually a mixture of at least two fragments, having polynucleotide sequences of hCMV strains and the clinical sample. The single stranded DNA fragments are allowed to complex with any DNA present in the clinical sample. Means are provided for detecting duplexing of the hCMV fragments to DNA present in the sample, generally involving hybridization of the nucleotide sequences in the sample with at least substantial complementarity to one or more of the hCMV fragments with the DNA present in the sample. The formation of duplexes is diagnostic of the presence of hCMV.

The hCMV fragments which serve as the diagnostic probes may be obtained by restriction endonuclease cleavage of the hCMV genome. Different restriction endonucleases may be used individually or in combination. Illustrative restriction endonucleases include EcoRI, HindIII and BglII. The fragments may range from about 20 b (bases) to 20 kb, usually 100b to 20 kb preferably from about 0.1 to 15 kb. While individual fragments may be employed, particularly those of over 2 kb, mixtures will be preferred. Fragments of from about 2 to 15 kb are particularly useful. The mixtures will generally have at least 2 fragments and not more than about 12 fragments, preferably from about 3 to 8 fragments.

The hCMV genome has regions of inverted repeats. The fragments are derived from the unique sequences of the long and/or short component designated L (long) or S (short).

The accompanying figure shows the restriction map with 3 restriction endonucleases. With EcoRI, the fragments obtained vary from about 0.8 kb to 17 kb.

The fragments which are selected for use in diagnosis are screened for cross-reactivity with human DNA and other viruses. The fragments which are employed should have only a minor, if any, amount of complementarity with the DNA of human cells and other viruses, while at the same time being able to detect the wide variety of strains of hCMV which have been detected in humans.

Of particular interest are combinations of fragments obtained with EcoRI, where the fragments are over 2 kb in length. These fragments or their equivalents (that is, fragments obtained with restriction enzymes other than EcoRI, which include a substantial portion of an EcoRI fragment e.g. greater than 40 percent, but do not include flanking regions which cross-hybridize with human DNA) may be combined so as to be capable of detecting all of the hCMV strains, yet not cross-hybridize with human DNA, so as to result in false positives. The EcoRI fragments which readily detect human DNA are E, F, H, P, R and b (F and H are junction fragments comprised of L +W and N +W respectively). Some detection of human DNA is also observed with EcoRI fragments A, C, I, O, V, c, d, e. The larger fragments B, D, G, J, K, S, T, and M are of particular interest and diagnostic compositions having at least one of these fragments (or their equivalent), usually at least two of these fragments are of particular interest.

The method of detection of the presence of the hybrid can be carried out in a wide variety of ways and is not a critical aspect of this invention. Rather, as new techniques are developed, they may be readily accommodated to the subject invention. One technique involves labeling of the fragments with a label which provides a detectible signal. Commonly, a radionuclide e.g. $^{32}P$ may be used to label the fragments, conveniently by nick translation.

Alternatively, rather than having a radionuclide, nucleotides can be provided which have a different label which allows for detection. One technique, is to have a biotin labeled nucleotide which becomes incorporated into the polynucleotide and serves, as a site for binding to avidin. The avidin can be labeled with a wide variety of labels, such as fluorescers, enzymes, radionuclides, substrates, or the like, to provide for a sensitive detection system.

For the most part, hybridization techniques involve having the DNA in the sample bound to a solid support and combined with a solution of labeled fragments., Various techniques may be employed for binding the DNA to a solid support e.g. binding to a nitrocellulose support with elevated temperatures; covalent linking with diazotized paper, etc.

For the most part, the samples which are employed will involve intact cells or cellular debris. The cells may be bound to a surface e.g. such as cellulosic or nitrocellulosic, by lysing of the cells by conventional means e.g. mild base, enzymatic, etc., followed by washing away of debris and fixing the DNA to the surface e.g. heating. Alternatively, the DNA from the cells may be isolated and cleaved, separated, by electrophoresis and then covalently bonded to a support. The fixed sample may then be combined with a solution of the labeled fragments under hybridization conditions.

Various techniques may be employed to enhance sensitivity. One technique is to employ flanking region(s) with the fragments having common DNA sequences which will not interfere with the hybridization of the hCMV fragments. Usually, the flanking regions will be of at least about 500 bases. This can be readily achieved by employing the cloned linear hCMV fragments, retaining at least a portion of the vector, the vector will be cloning vectors capable of replication in a unicellular microorganism. By cleaving the plasmids with a restriction endonuclease at a common site in the vector, hybridization can involve extensive oligomerization of the labeled DNA for each duplex which forms between the labeled hCMV fragment and the sample DNA bound to a support.

Conveniently, the plasmids may be nick translated using radionuclide labeled nucleotide triphosphate and optionally ligated and cleaved with a restriction endonuclease. DNA probe concentrations may be employed with as low as 1-5 ng DNA/ml and hybridization times of from about 1 to 5 hours to detect hCMV.

For the most part, the DNA probes will be prepared by cloning fragments obtained from hCMV, so that once fragments are obtained from the virus and cloned, the virus is no longer required. Individual fragments may be joined to provide larger fragments or cut to produce smaller fragments.

Stringent conditions are employed for the hybridization, such as elevated temperatures, generally from about 35° to 70° C., high ionic strength, having salt concentrations of from about 0.05 to 2M by employing various inert salts e.g. NaCl, as well as by varying the pH, generally providing a pH in the range of about 5 to 10. Various buffers may be employed. Also, organic solvents may be employed up to about 60 volume percent e.g. N,N-dimethyl formamide.

Other materials may also be included in the assay medium, such as stabilizers, nuclease inhibitors dextran sulfate chelating agents e.g. citrate, EDTA, etc.

The mixture is then incubated for a sufficient time to allow hybridization to occur. Generally, the incubation will take at least about one hour and will usually not be more than 5 days, generally ranging from about 2 to 72 hrs.

The fixed DNA may then be separated from the hybridization solution, washed to remove any non-specific binding, and the presence of any label as a result of duplexing determined.

The samples which are employed may come from a wide variety of physiological clinical samples, including urine, blood, smears, tissue sections, or the like. These cells may be pretreated in a variety of ways or be applied directly to the surface to which the DNA is to be bound. With blood, buffy coat screening may be employed.

The following examples are offered by way of illustration and not by way of limitation.

MATERIAL AND METHODS

Virus and cells hCMV strain AD169 was obtained from the American Type Culture Collection. Virus titers were determined by plaque assay (Wentworth and French, Proc. Soc., Exp. Biol. Med. (1970) 135:253–258). Human embryonic lung cells (obtained from Stephen Spector) were grown in Dulbecco modified Eagle medium containing 10% calf serum, L-glutamine (0.292mg/ml), penicillin-streptomycin (0.2mg/ml; Irvine Scientific), Amphotericin B (3μg/ml; Irvine), and gentamicin 50μg/ml; Schering Corp.). Infection was carried out at a multiplicity of infection of 0.05 to minimize the production of defective virus. When 80% of the cells showed cytopathic effect, [$^3$H]thymidine (5μCi/ml; Amersham Corp.) was added, and the calf serum reduced to 3%.

Preparation of the viral DNA

Four to five days after the addition of label, extracellular virus was harvested from the medium. The cell debris was removed by low-speed centrifugation, and the virus was precipitated with polyethylene glycol as described by Hamelin and Lussier (J. Gen. Virol. (1979) 42:193–197). The virus was pelleted by centrifugation for 1 hr. at 19,000 rpm in a Beckman 19 rotor at 4° C. The pellets, suspended in DNA buffer (0.1M NaCl, 0.01M Tris, and 0.01M EDTA, pH8) containing 10% sorbitol (wt/vol), were centrifuged through a sorbitol step gradient (75, 48, and 20% sorbitol) for 1 hr. at 20° C. and 26,500 rpm in a Beckman SW27 rotor. Fractions comprising the viral peak (at the interface of the 48 and 75% sorbitol layers) were pooled, diluted with 0.15M NaCl–0.05M Tris, pH7.2, and centrifuged for 3hr. at 26,500 rpm, 20° C., in a Beckman SW27 rotor. The viral pellet was suspended in DNA buffer containing 1% sodium dodecyl sulfate (SDS), treated with RNase A (50μg/ml; Boeringer Mannheim Corp.) and pronase (1mg/ml; Calbiochem) at 37° C. for 1 hr., and extracted twice with 2 volumes of phenol-chloroform-isoamyl alcohol (50:48:2) and twice with 2 volumes of chloroform-isoamyl alcohol (96:4). Two equilibrium cesium chloride centrifugations were performed, using an initial cesium chloride density of 1.72g/ml. The gradients were centrifuged at 38,000 rpm for 60hr. in a Beckman Ti60 rotor. Fractions containing the viral DNA (banding at a density of 1.716g/ml) were combined and dialyzed against 5mM Tris-0.1 mM EDTA, pH7.2. The purity of the isolated DNA was assessed as previously described (Tamashio and Spector (1980) In B. N. Fields, et al. (ed.) Animal virus genetics, ICN-UCLA Symposia on Molecular and Cellular Biology, vol. XVIII, Academic Press, Inc., New York.)

Construction, transfection, screening, and isolation of recombinant plasmids

The plasmid pACYC184, which contains tetracycline and chloramphenicol resistance markers (Chang and Cohen, J. Bacteriol. (1978) 134:1141–1156), was extracted from bacteria and purified by equilibrium cesium chloride-ethidium bromide centrifugation by the method of Kahn et al. (Methods Enzymol. (1980) 68:268–280). Plasmid and hCMV DNA were cleaved with the restriction endonuclease EcoRI in 0.1 M Tris, 0.05M NaCl, 0.005M $MgCl_2$ and 0.05% Nonidet P-40, pH7.5, at 37° C. for 1 hr. followed by inactivation of the enzyme at 65° C. for 10min. EcoRI-cleaved plasmid was treated with bacterial alkaline phosphatase (Millipore Corp.) at a concentration of 2 U per μg of DNA in 0.01M Tris-0.1% SDS, pH9.5, for 1 hr. at 65° C. to prevent recircularization of the plasmid alone. The reaction mixture was extracted twice with 2 volumes of phenol and twice with 2 volumes of ether. The DNA solution was adjusted to 0.2M NaCl and precipitated by the addition of 2 volumes of 95% ethanol. Viral EcoRI restriction fragments were ligated to the cloning vehicle by incubating 1μg of hCMV DNA, 0.25μg of pACYC184, and 2.5 U of DNA ligase (Bethesda Research Laboratories) at 4° C. in ligase buffer (0.02M Tris, 0.01M $MgCl_2$, 0.01M dithiothreitol, and 0.03M NaCl, pH7.6) containing 0.001M ATP for 36 hr. (total volume of 25μl ). In some experiments, the viral EcoRI fragments were fractionated by size before ligation to plasmid. In these cases, the EcoRI fragments were subjected to electrophoresis through 0.8% Seaplaque agarose (Marine Colloids) in buffer containing 40mM Tris, 20mM sodium acetate, 18mM NaCl, and 2mM EDTA, pH8, and the bands were visualized by transillumination after staining with ethidium bromide. The gel slice containing the desired band was then melted at 65° C. in 10 volumes of 0.3M NaCl, 10mM EDTA, and 10mM Tris, pH7.2, and loaded onto a benzoyl-naphthol-DEAE (BND)-cellulose column (Serva, Heidelberg) which was maintained at 45° C. The column was washed extensively with loading buffer to remove the agarose, and the DNA was eluted with buffer containing 1M NaCl, 1% caffeine, 10mM EDTA, and 10mM Tris, pH7.2.

Transfection of the ligated plasmid into *E. coli* strain HB101 RecA⁻ was done by the $CaCl_2$-RbCl method of Kushner ((1978) In H. W. Boyer and S. Nicosia (ed.), Genetic Engineering. Elsevier/North-Holland Biomedical Press, Amsterdam). Bacterial colonies containing pACYC184 were selected on agar plates containing 5 to 20μg of tetracycline per ml and were tested for sensitivity to 25μg of chloramphenicol per ml. Since EcoRI cleaves within the chloramphenicol resistance marker of the plasmid, bacteria containing recombinant plasmid should be sensitive to chloramphenicol.

The selected clones were grown overnight with shaking at 37° C. in 5 -ml cultures of D medium (15mM $KH_2PO_4$, 40 mM $K_2HPO_4$, 8mM $(NH_4)_2SO_4$, 0.4mM $MgSO_4$, 2mM sodiux: citrate, 0.5% Casamino Acids, 5mg of glucose per ml, 10μg of thiamine per ml, and 5μg of tetracycline per ml). A portion from these cultures was mixed with an equal volume of glycerol and placed at −20° C. for storage. An inoculum from the 5 -ml cultures was diluted 1:50 into 35 ml of D medium and incubated at 37° C, with shaking, until the cultures reached an optical density at 350 nm of 0.3 to 0.35. Chloramphenicol (4.5ml of a 1mg/ml solution in D medium) was then added to amplify the plasmid DNA, and the cultures were incubated at 37° C., with shaking, overnight. The recombinant plasmids were isolated by the rapid purification method of Kahn et al., supra, which involves treatment of the bacteria with lysozyme and detergent and a high-speed centrifugation to separate cell debris and chromosomal DNA from the plasmid.

Methods used in characterization of cloned inserts

The following restriction enzymes were used in characterizing the cloned inserts: EcoRI, HindIII, BamHI, BglII, and PvuII. All restriction endonucleases with the exception of EcoRI were obtained from New England Biolabs and were used in the buffer recommended by the supplier. All incubations were carried out at 37° C. for 1 hr. followed by inactivation at 65° C. for 10min. Restriction fragments were separated on 0.8% agarose gels, using the same buffer system as the Seaplaque agarose gels. DNA was transferred from gels to nitrocellulose filters by the method of Southern (J. Mol. Biol. (1975) 98:503–517)

DNA was $^{32}P$ labeled by nick translation Rigby et al, J. Mol. Biol. (1977) 113:237-251) with DNA polymerase I (Bethesda Research Laboratories) and $[\alpha\text{-}^{32}P]dCTP$ or end labeled by treatment with polynucleotide kinase (Bethesda Research Laboratories) in the presence of $[\gamma\text{-}^{32}P]ATP$ (ICN). In preparation for end labeling, purified hCMV DNA was cleaved with EcoRI, extracted twice with phenol and twice with ether, and precipitated with ethanol as described above. The viral fragments were treated with bacterial alkaline phosphatase, and the reaction mixture was extracted with phenol and ether and subjected to ethanol precipitation. The reaction with kinase was performed by incubating the DNA with 12 U of T4 polynucleotide kinase in 50mM glycine, pH9.5, 10mM $MgCl_2$, 5mM dithiothreitol, 25% glycerol, and 0.2mM spermidine at 37° C. for 1 hr. The reaction was inactivated at 65° C. for 10 min, diluted with 4 volumes of DNA buffer, and loaded onto a Sephadex G-75 column to separate the labeled viral fragments from free label. Fractions containing the labeled DNA were combined and precipitated in ethanol, using salmon sperm DNA as carrier. The sample was suspended in 5mM Tris-0.1 mM EDTA, pH7.2, and stored at 4° C. Hybridization of nick-translated DNA to Southern filters was accomplished by incubating the filters at 37° C. for 16 hr. in 50% formamide, 50mM N-2-hydroxyethylpiperazine-N'-2-ethanesulfonic acid (HEPES), pH7.0,1×Denhardt (0.02% each of polyvinylpyrrolidone, Ficoll, and bovine serum albumin), 3 x SSC (1×SSC=0.15M NaCl plus 0.015M sodium citrate), 0.1 mg of salmon sperm DNA per ml, and 10mM EDTA followed by hybridization with labeled DNA in the same buffer at 37° C. for 4 to 5 days. After hybridization, filters were washed in 2×SSC for 1 hr; and several rinses with 0.1×SSC at room temperature.

Colony hybridization

A modification of the method of Grunstein and Hogness (Proc. Natl. Acad. Sci. USA (1975) 72:3961-3965) was used in the colony hybridizations. Colonies were grown on agar plates containing tetracycline (5μg/ml) and rubbed onto Whatman 541 filters. The filters were placed sequentially, for the period of time indicated, on Whatman 3MM paper saturated with each of the following buffers:0.5N NaOH, 7 min; 1.0M Tris, pH7.4, 5 min minimum. Each filter was then placed on the vacuum apparatus described by Grunstein and Hogness, supra. A vacuum was applied for 2 min, 95% ethanol (1 ml per $cm^2$ of filter) was passed through the filter by vacuum filtration, and the filter was air dried on Whatman 1MM paper. The filters were baked at 80° C. for 2hr. in a vacuum oven and hybridized with appropriate probes in the same manner as Southern filters.

Cells, viruses and purification of hCMV and cellular DNA

The procedures for growing human embryonic lung cells, infecting the cells with hCMV strain AD169, and purifying the viral DNA have been described by Tamashiro et al. (J. Virol. (1982) 42:547-557). To prepare $^{32}$P-labeled hCMV DNA, infected cells were exposed to 50μCi of $^{32}PO_4$ per ml in low-phosphate (0.01mM sodium phosphate) Earle minimal essential medium supplemented with 3% dialyzed calf serum for 4 days before harvesting the extracellular virus. High molecular weight uninfected and infected cell DNA was extracted according to procedures described by Hughes et al. (Cell (1979) 18:347-359). The high molecular weight intracellular hCMV DNA was purified from infected human embryonic lung cells 4 to 5 days after the cells showed 80% cytopathic effect and was enriched for viral sequences by isopycnic cesium chloride centrifugation. The equilibrium density of hCMV DNA (1.716g/ml) differs sufficiently from that of human cell DNA (1.699g/ml) to permit separation of the viral DNA from the majority of the cell sequences.

Growth, purification, and labeling of hCMV DNA from recombinant DNA clones

Colonies of *Escherichia coli* strain HB101 containing recombinant hCMV plasmids were picked from a freshly streaked agar plate into 100 ml of nutrient broth containing tetracycline (20μg/ml) and grown overnight at 37° C. Bacterial pellets were prepared by centrifugation of the culture at 6,000 rpm for 5min in an RC-5 low-speed centrifuge at 4° C. Each pellet was suspended in 7.5 ml of 25% sucrose, 50mM Tris-hydrochloride, pH8.0, and 2.5 ml of lysozyme (10 mg/ml) in 25% sucrose-50 mM Tris hydrochloride, pH8.0, was added. The mixture was swirled gently and placed on ice for 15 to 30 min, and 3.5 ml of 0.25 M EDTA, pH8.0, was then added slowly. After the lysate was placed on ice for an additional 10 to 12 min, 3.75 ml of 2% Sarkoxyl in TES (50 mM Tris-hydrochloride, pH8.0, 50 mM NaCl, and 5 mM EDTA)was added, and the lysate was kept on ice for 15 to 45 min. The volume was then adjusted to 22.5 ml with TES, and CsCl (23.1 g) was added. After the addition of 2.5 ml of ethidium bromide (5 mg/ml) in TES, the mixture was centrifuged to equilibrium, using a Ti60 rotor as 40,000 rpm for 60 hr at 20° C. The superhelical recombinant plasmid DNA was collected, the ethidium bromide was removed by successive extractions with isoamyl alcohol, and the solution was dialyzed against 5 mM Tris-hydrochloride00.1 mM EDTA, pH 7.2. The isolated recombinant plasmids were then cleaved with EcoRI restriction endonuclease, and the fragments were separated by electrophoresis through 0.8% Sealplaque agarose (gels buffered wit TEA [40 mM Tris-hydrochloride, 20 mM sodium acetate, 18 mM NaCl, and 2 mM EDTA, pH8.1]) to separate the plasmid from the hCMV insert. The band containing the EcoRI hCMV DNA fragment was excised from the gel and purified away from the Seaplaque agarose according to the procedure described in Tamashiro et al, supra. To label the DNA to a high specific activity ($\sim 10^8$ cpm/μg) with [$^{32}$P]dCTP, the nick translation procedure of Rigby et al., supra, was used.

Digestion of hCVM DNA with restriction endonucleases and electrophoresis of the DNA samples Purified cytomegalovirus DNA was digested to completion with the restriction endonucleases EcoRI, BglII, or HindIII as described by Tamashiro et al., supra. High-molecular weight infected cell DNA enriched for hCMV sequences was digested partially with EcoRI endonuclease. The extent of the digestion was monitored by removing a small portion of the reaction, which was then added to a tube containing 1μg of lambda DNA. The test samples were incubated in parallel with the digests containing only hCMV DNA for 1 hr. at 37° C. To terminate the reactions, all samples were heated to 65° C. for 10 min. The test samples were analyzed by electrophoresis in 0.8% agarose gel, and the DNA was visualized by staining with ethidium bromide followed by transillumination with a UV light source. The reactions were judged to be complete if only the appropriate set of restriction fragments for lambda DNA were observed.

The hCMV DNA samples were analyzed by electrophoresis in 0.8% Seakem agarose preparative slab gels (5 mm thick) buffered with TEA. Gels were formed in a horizontal gel box (12.5 by 28 cm), and the samples were subjected to electrophoresis for 16hr. at 50 to 75mA. The unlabeled hCMV DNA samples were placed in a slot 9.5 cm wide. A parallel lane contained hCMV DNA uniformly labeled with $^{32}$P and cleaved to completion with EcoRI, HindIII, or BglII.

Hybridization procedures

After electrophoresis through agarose, the hCMV DNA was denatured, neutralized in situ, and transferred to nitrocellulose sheets (0.45μm by 12.5cm by 20cm) according to the procedure of Southern, supra. The filters were then baked (80° C. in vacuo) and cut into parallel strips 3.4 mm wide. Each strip was preannealed overnight at 37° C. in 50% formamide, 3×SSC (1 x SSC =0.15M NaCl plus 0.015M sodium citrate), 50μg of denatured salmon sperm DNA per ml, 10mM EDTA, 50mM N-2-hydroxyethylpiperazine-N'-2-ethanesulfonic acid (HEPES) (pH7.0), and 1×Denhardt's reagent (0.02% each of bovine serum albumin, Ficoll, and polyvinylpyrrolidone). The filters were then annealed in the same buffer to individual nick-translated $^{32}$P-labeled cloned hCMV DNA fragments at 37° C. for 96 hr. After hybridization, unannealed DNA was removed by washing the filters once with 2×SSC at room temperature for 1 hr. twice with 0.1×SSC-0.1% sodium dodecyl sulfate for a total of 1 hr. at 55° C., and five to eight times in rapid succession with 0.1×SSC at room temperature. The filter strips were dried, placed in exact parallel with other strips cut from the original filter, and subjected to autoradiography in the presence of a Lightning Plus intensifying screen at −70° C. The filter strip containing the hCMV DNA uniformly labeled with $^{32}$P and cleaved with the same restriction endonuclease allowed identification of each of the hybridized bands. In some cases, hCMV restriction endonuclease fragments were also used that were endlabeled with [γ-$^{32}$P]ATP and kinase as described above.

To rapidly characterize the recombinant hCMV DNA clones with respect to any homology with uninfected cell DNA, a "dot-blot" hybridization method was employed.

Spotting DNA onto nitrocellulose filters

The DNA samples are resuspended in 5–10μl of buffer containing 10mM Tris, 10mM EDTA pH7.2. The nitrocellulose paper (Schleicher and Schuell BA 85) is cut into strips 1.5 cm wide and long enough to spot samples 1.5 cm apart. The nitrocellulose is soaked first in distilled H$_2$O just to wet and then equilibrated in 20×SSC (1×SSC=0.15M NaCl 0.015M Na citrate) for 15 min. The filters are dried with a heat lamp. The 5–10μl samples are denatured at 100° C. for 4 min., quick chilled on ice and spotted onto the dry paper in a tiny spot; this is best achieved by spotting 2μL at a time. The filters are then dried with a heat lamp and baked 2 hr. at 80° C. in a vacuum oven. After baking the filters may be stored in a desiccator at 4° C. Before hybridization the filters are prehybridized with buffer (100μl/cm$^2$ of filter) containing 50% formamide, 5×Denhardt's reagent, 5×SSC, 0.1% SDS, 10mM EDTA, 10mM Hepes, pH7.2 and 100μg/ml of heterologous DNA (salmon sperm or E. coli DNA) at 46° C. for 1-12 hours with shaking. For prehybridization and hybridization a seal-a-meal bag, sealed with all air removed or Saran Wrap folded securely may be used to hold the filter and buffer. These packets are then wrapped in aluminum foil.

Spotting DNA onto activated diazotized paper (DBM paper—Schleicher and Schuell)

This method provides for the covalent attachment of the DNA sample onto paper filters. Schleicher and Schuell Trans-Bind ABM paper (aminobenzyloxymethyl paper) is used. The paper is stored in a bag sealed with nitrogen 5 at −20° C. ABM filter strips 1.5 cm wide and long enough to spot samples 1.5 cm apart are cut and placed in ice cold 1.2M HCl (0.5ml/cm$^2$ of paper). For each 10 ml of HCl is added 0.3 ml of a freshly prepared solution of 10 mg/ml sodium nitrite. The paper is shaken in this solution for 30 min. at 4° C. The paper is washed twice with ice-cold distilled H$_2$O and twice with 0.2M sodium acetate buffer pH4.0. For spotting the DNA, the activated ABM paper (DBM paper) is placed on top of Whatman 3mM paper equilibrated in 0.2M acetate buffer pH4.0 in a suction box with very gentle suction applied. The DNA samples resuspended in 5–10μl of 10mM Tris, 10mM EDTA pH7.2 are denatured by heating to 100° C. for 4 mins., quick-cooled on ice, and spotted onto the DBM paper in as tiny a spot as possible. After transfer, the DBM paper is soaked in 0.5M NaOH for 30 min. at room temperature to inactivate any remaining diazonium groups. The paper is then washed in 2×SSC, 0.1% SDS. Before hybridization the filter may be stored at 4° C. in hybridization buffer containing 50% formamide, 5×Denhardt's reagent, 5×SSC, 0.1% SDS, 10mM EDTA, 10mM Hepes, and 100μg/ml of heterologous DNA (salmon sperm or E. coli DNA).

Hybridization Conditions

The nitrocellulose filters, already prehybridized, or DBM paper stored in hybridization buffer are placed in buffer (50–100μl/cm$^2$ of filter) containing 50% formamide, 5 ×Denhardt's reagent, 5×SSC, 0.1% SDS, 10mM EDTA, 10mM Hepes, pH7.2, 100μg/ml heterologous DNA and $^{32}$P-labeled cloned CMV DNA probe (10$^5$ cpm—5×10$^5$ cpm/cm$^2$ of filter); and optionally containing 10% dextran sulfate; DNA is labeled to a specific activity of 5×10$^8$–5×10$^9$ cpm/μg by nick-translation (Rigby et al., J. Mol. Biol. 113, 237–251, 1977) with 1 or 2 $^{32}$P-deoxytriphosphates of specific activity 3000Ci/mM. The filters and hybridization buffer with labeled probes are placed in a seal-a-meal bag, sealed with all air removed, or in Saran Wrap ® folded securely. The packets are then wrapped in a aluminum foil and incubated for 15 to 72 hours at 46° C. Most hybridization is complete by 15 hours but there in no harm in letting the filters incubate for 72 hours. After hybridization the filters are washed in 2×SSC, 0.1% SDS (23° C.) followed by several changes of 0.1×SSC, 0.1% SDS at 50° C. for 1 hour, and then in several changes of 0.1 x SSC (23° C.). The filters are dried and exposed for autoradiography in the presence of Dupont Cronex Lightning Plus Intensifying Screens at −70° C.

Nucleic acid was extracted from cells of several species and samples containing 5μg DNA were spotted on nitrocellulose filters and hybridized as described above with each of the 32 EcoRI subgenomic fragments labeled with $^{32}$P-dCTP by nick translation. For standardization, each of the labeled viral fragments were hybridized to 1 ng of purified hCMV virion DNA spotted onto nitrocellulose filters. After hybridization, the nitrocellulose filters were washed under stringent conditions and subjected to autoradiography. Six of the 32 cloned viral fragments showed hybridization to uninfected human DNA samples. These were EcoRI fragments E, F, H, P, R and b, which are fragments from the unique long region of the genome and in the case of fragments F and H from the junctions of the long and short regions of the genome. The four fragments R, b, F and H also hybridized to DNA from mouse, chicken and sea urchin, but not to DNA from B. subtilis or lambda phage. There is also some detection of human DNA with EcoRI fragments A, C, I, O, V, c, d and e. None of these fragments should be employed in the detection of the hCMV.

Based upon relative intensities, the degree of nucleotide base pairs of homology was estimated at 7000 nucleotide base pairs per haploid genome for fragment R (5.8kb) and P (6.7kb). The degree of homology was estimated at about 3500 nucleotide base pairs per haploid human genome for the other fragments b (2.9kb), E (15.6kb), F (about 13 kb), and H (about 11.8kb). These numbers represent minimal estimates. The level of sensitivity was greater for the smaller fragments.

Under the subject assay conditions, the lower limit for number of nucleotides base pairs of homology which could have been detected ranged from 100 (for the smallest fragment of 0.8 kb) to 1500 (for the largest fragment of 17 kb). The recombinant hCMV cloned were then tested to assess homology for each clone which had DNA extracted from 6 clinical isolates of CMV and the AD169 strain. The clinical isolates were obtained from the urines of patients with the following diagnosis: 1 infant with congenital CMV; 4 infants with hospital acquired CMV; and 1 child with a histiocytic malignancy.

Nucleic acid was extracted from CMV infected human embryonic lung fibroblast cells and purified from cellular DNA by equilibrium centrifugation through cesium chloride. Using the dot-blot hybridization technique, 100 ng CMV DNA were spotted on nitrocellulose filters and hybridized with each of the 32 subgenomic fragments labeled with $^{32}$P-dCTP by nick translation. Thirty-one of the 32 cloned viral fragments hybridized to all clinical CMV isolates studied. Only fragment "h" failed to hybridize to any of the isolates studied.

In accordance with the subject procedure, the method allows detection of $10^5$ particles of virus. These experiments used as hybridization probes individual subgenomic cloned fragments labeled by nick translation with $^{32}$P-deoxytriphosphates to a specific activity of $5 \times 10^7$ to $10^8$ CPM/$\mu$g. However, by labeling a fragment with two high activity deoxynucleotide triphosphates (each about 300Ci/mM) coupled with modified hybridization conditions (5–10×Denhardt's solution instead of 1×Denhardt's), the sensitivity can be increased 10–15 fold to detect approximately $10^4$ particles of CMV. By employing mixtures of CMV fragments, further enhancement of the sensitivity can be achieved.

In studying urines, the virus and cells in urine are pelleted by high speed centrifugation and the DNA extracted by standard techniques. The DNA is then dotted onto a nitrocellulose filter, hybridized against a mixture of cloned DNA probes lacking cell-related DNA sequences and identified by autoradiography. This technique has successfully identified CMV positive and CMV negative urines, where the positive urines had infectious virus titers of from $10^3$ to $10^4$ per ml.

The conditions used for the hybridization involved employing cell DNA samples which were extracted with phenol and chloroform after digestion with pronase and SDS and the DNA concentration determined by diphenylamine assay. $^{32}$P-labeled probes ($10^6$cpm) were then hybridized with DNA on nitrocellulose filters at 46° C. for 16 hours. Filters were washed as described above.

The above results demonstrate that a sensitive accurate assay can be performed for the detection of CMV in the presence of foreign DNA. Thus, cells suspected of having CMV may be lysed and the resulting DNA contacted with single stranded probes under stringent hybridization conditions and the formation of duplexes determined. By providing for an appropriate mixture of fragments of relatively small size, the test can be rapidly performed with a high degree of accuracy.

Although the foregoing invention has been described in some detail by way of illustration and example for purposes of clarity of understanding, it will be obvious that certain changes and modifications may be practiced within the scope of the appended claims.

What is claimed is:

1. A method for determining the presence of human cytomegalovirus ("hCMV") or portions thereof in a clinical sample suspected of containing hCMV DNA, said method comprising: combining under hybridizing conditions of predetermined stringency said sample and at least one single stranded DNA fragment of human cytomegalovirus having at least 20 bases, which fragment is non-cross-hybridizing with human DNA; and determining the formation of duplexes between any of said DNA fragments and said sample DNA as diagnostic of the presence of CMV in said sample.

2. A method according to claim 1, wherein prior to said combining, any DNA in said clinical sample is bound to a solid support.

3. A method according to claim 1, wherein said clinical sample contains cells suspected of containing human cytomegalovirus, which includes the additional steps of prior to said combining, lysing cells in said sample to release DNA from said cells; and affixing said sample DNA to a solid support.

4. A method according to either of claims 2 or 3 wherein said support is cellulosic or nitrocellulosic.

5. A method according to claim 1, wherein said at least one cytomegalovirus fragment has at least one flanking region of at least about 500 bases, said flanking region being non-cross-hybridizing with human DNA.

6. A method according to claim 5, wherein said at least one fragment has from about 2 kb to about 20 kb.

7. A method according to either of claims 1 or 6, wherein said at least one fragment is labeled with a radionuclide.

8. A method for determining the presence of human cytomegalovirus ("hCMV") in a human host by assaying for hCMV DNA in a clinical sample, said method comprising:

combining under hybridizing conditions of predetermined stringency said sample in a mixture of at least two different single-stranded DNA fragments of hCMV, each of at least about 100 bases, with at least one fragment over 2kb, wherein said fragments are non-cross-hybridizing with human DNA and are selected from the group consisting of EcoRI restriction fragments a, g, i, B, D, G, J, K, M, Q, S, T, U, X, and Y and fragments duplexing with said restriction fragments and non-cross hybridizing with human DNA; and determining the formation of duplexes between said DNA fragments and DNA in said sample as diagnostic of the presence of hCMV in said sample.

9. A method according to claim 8, wherein cellular DNA in said sample is separated and any remaining DNA in said sample is bound to a solid support prior to combining.

10. A method according to claim 8, wherein said restriction fragments have a flanking region of at least 500 bases which is non-cross hybridizing with human DNA.

11. A method according to claim 10, wherein said flanking region is derived from a cloning vector replicable in a unicellular microorganism.

12. A method according to any one of claims 8,9,10 or 11 wherein said fragments are labeled with a radionuclide.

13. A DNA composition useful for detecting human cytomegalovirus ("hCMV") consisting essentially of at least one single-stranded fragment of hCMV of at least 100 bases selected from the group consisting of EcoRI restriction fragments a, g, i, B, D, G, J, K, M, Q, S, T, U, X, and Y and fragments duplexing with said restriction fragments and non-cross-hybridizing with human DNA.

14. A composition according to claim 13, wherein said fragments have at least one flanking region of at least 500 bases non-cross-hybridizing with human DNA.

15. A composition according to claim 14, having at least two different fragments, at least one fragment being of 2 kb.

16. A composition according to claim 13, having at least two different fragments, at least one fragment being of at least 2 kb.

17. A composition according to any one of claims 13, 14, 15 or 16, wherein said fragments are labeled with a radionuclide.

18. A method for determining the presence of human cytomegalovirus ("hCMV") in a human host by assaying for hCMV DNA in a clinical sample, said method comprising:

combining under hybridizing conditions of predetermined stringency said sample and a mixture of at least two different single-stranded DNA fragments of hCMV, each of from about 2 kb to about 15 kb, wherein said fragments are non-cross-hybridizing with human DNA and are selected from the group consisting of EcoRI restriction fragments B, D, G, J, K, M, S, and T and fragments duplexing with said restriction fragments and non-cross hybridizing with human DNA; and determining the formation of duplexes between said DNA fragments and DNA in said sample as diagnostic of the presence of hCMV in said sample.

19. A method according to claim 18, wherein fragments B and D are combined with said sample.

20. A composition useful for detecting human cytomegalovirus consisting essentially of at least two different single-stranded fragments of hCMV DNA each of from about 2 kb to about 20 kb selected from the group consisting of EcoRi restriction fragments. B, D, G, J, K, M, S, T and fragments duplexing with said restriction fragments and non-cross-hybridizing with human DNA and having no flanking region or a flanking region which does not hybridize with human DNA and is derived from cloning of said restriction fragment.

21. A composition according to claim 20, wherein said fragments are B and D.

22. The method of claim 18 wherein said clinical sample comprises buffy coat.

* * * * *